(12) United States Patent
Bunker

(10) Patent No.: US 10,780,015 B2
(45) Date of Patent: Sep. 22, 2020

(54) METHOD AND APPARATUS FOR VISUAL TRAINING

(71) Applicant: AMBLYOPTICA (HOLDING) PTY LTD, Milton (AU)

(72) Inventor: Christopher Bunker, Birkdale (AU)

(73) Assignee: Amblyoptica Holding Pty Ltd (AU)

( * ) Notice: Subject to any disclaimer, the term of this patent is extended or adjusted under 35 U.S.C. 154(b) by 998 days.

(21) Appl. No.: 14/392,260

(22) PCT Filed: Jun. 25, 2014

(86) PCT No.: PCT/AU2014/050091
§ 371 (c)(1),
(2) Date: Dec. 24, 2015

(87) PCT Pub. No.: WO2014/205515
PCT Pub. Date: Dec. 31, 2014

(65) Prior Publication Data
US 2016/0184170 A1    Jun. 30, 2016

(30) Foreign Application Priority Data

Jun. 25, 2013 (AU) ................................ 2013902315

(51) Int. Cl.
*A61H 5/00* (2006.01)

(52) U.S. Cl.
CPC ......... *A61H 5/00* (2013.01); *A61H 2205/024* (2013.01)

(58) Field of Classification Search
CPC ............... A61H 5/00; A61H 2205/024; A61H 2201/5097; A61H 2201/1607; A61H 2201/165; A61H 2201/5007; A61B 3/0091; A61B 3/10; A61B 3/18; G02C 7/16; A61F 9/00
See application file for complete search history.

(56) References Cited

U.S. PATENT DOCUMENTS

| 5,452,027 | A | 9/1995 | Tylec |
| 8,454,159 | B1 | 6/2013 | Cislo |

(Continued)

FOREIGN PATENT DOCUMENTS

GB         201216600      * 10/2012  ............... A61H 5/00

OTHER PUBLICATIONS

PCT Search Report dated Sep. 9, 2014 for PCT/AU2014/050091 filed on Jun. 25, 2014 entitled Method and Apparatus for Visual Training.

*Primary Examiner* — Quang D Thanh
(74) *Attorney, Agent, or Firm* — Fish IP Law, LLP

(57) ABSTRACT

An apparatus for use in visual training of a subject, the apparatus including an at least partially opaque elongate occluder for at least partially occluding a substantially laterally oriented area of a field of view of a first eye so as to define an occluded area and a non-occluded area, and, wherein in use the occluded area moves relative to the field of view, and the subject views: at least one target that extends into the occluded area using both eyes so that the subject perceives an image of the target, the image in the non-occluded area being at least partially based on signals from the first eye and the image in the occluded area being at least partially based on signals from a second eye; and, ensures the target is at least partially aligned in the occluded and non-occluded areas.

15 Claims, 11 Drawing Sheets

(56) References Cited

U.S. PATENT DOCUMENTS

| | | | |
|---|---|---|---|
| 2001/0050754 A1 | 12/2001 | Hay et al. | |
| 2007/0200927 A1* | 8/2007 | Krenik | A61B 3/032 348/47 |
| 2008/0055541 A1 | 3/2008 | Coulter et al. | |
| 2015/0219929 A1* | 8/2015 | Silver | A61H 5/00 351/45 |
| 2016/0026009 A1* | 1/2016 | Urbajs | G02C 7/101 349/13 |
| 2018/0055717 A1* | 3/2018 | Lange | A61H 5/00 |

* cited by examiner

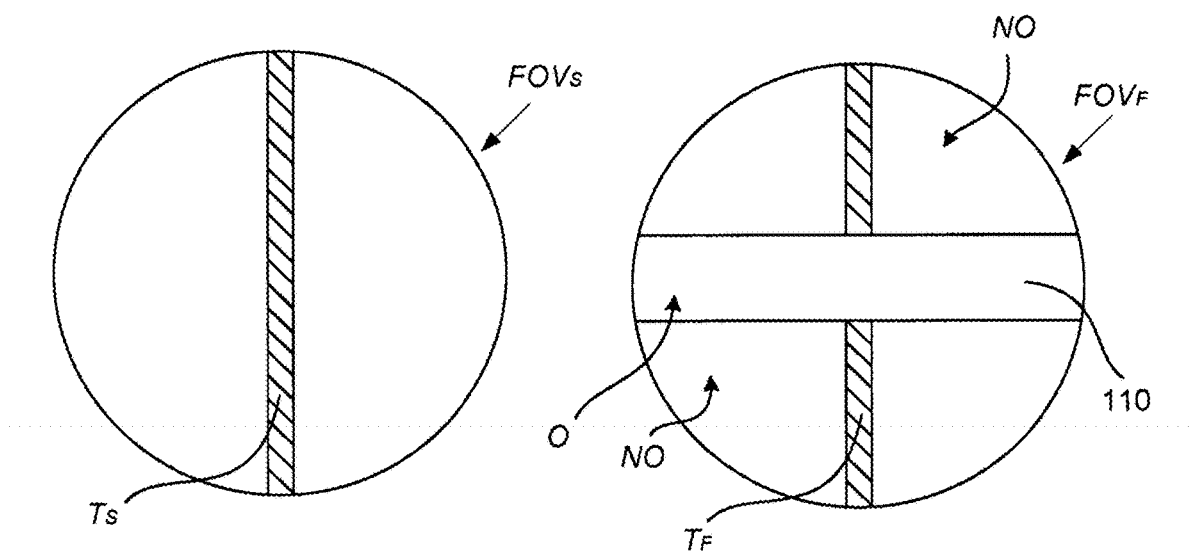
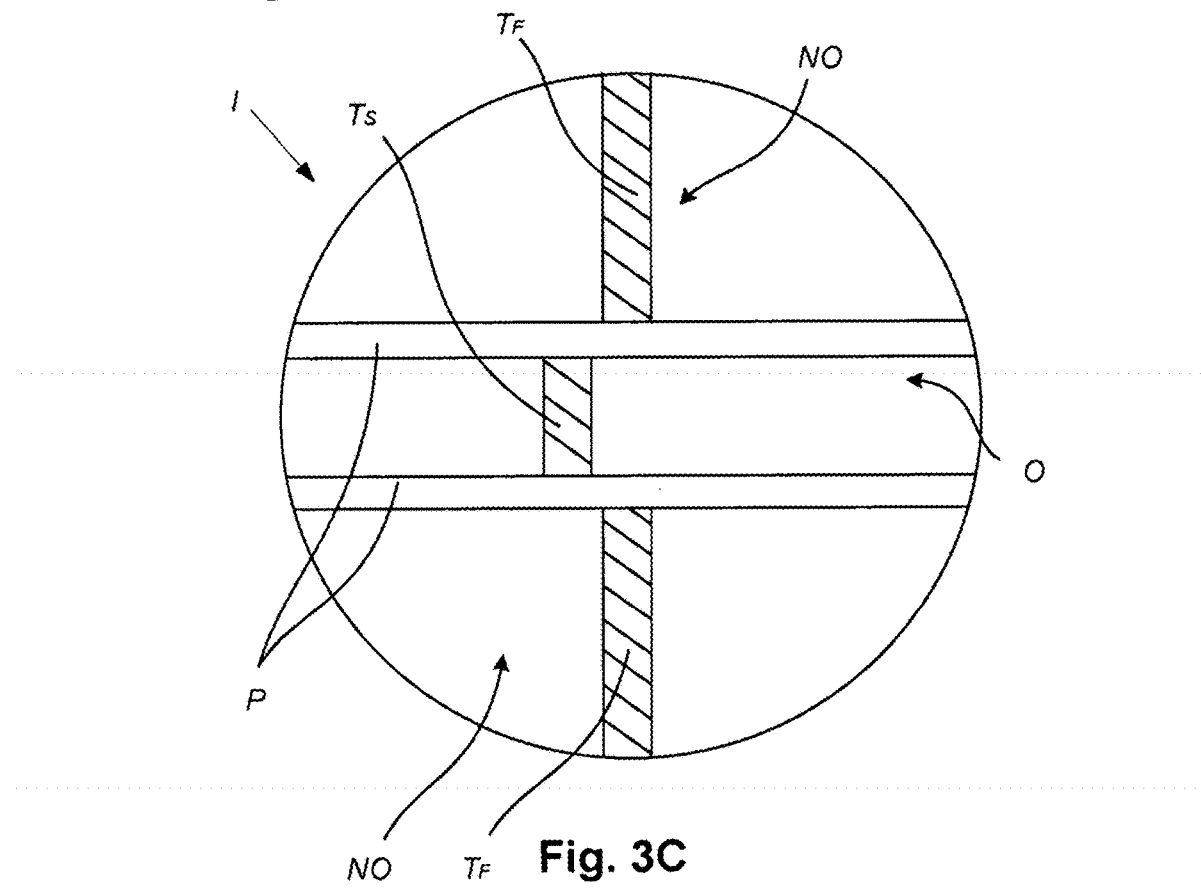

METHOD AND APPARATUS FOR VISUAL TRAINING

BACKGROUND OF THE INVENTION

The present invention relates to a method and apparatus for visual training, and in one example, for the treatment of amblyopia.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Amblyopia is a defect in vision which occurs during the development of the entire eye and brain 'seeing' system. It apparently occurs when, during the development of vision, the system is unable to use both eyes simultaneously for stereoscopic vision; amblyopia afflicts roughly three percent of children. The amblyopia is a response to a cause; the cause is some problem with presenting the brain with information from the two eyes in a way that the brain can learn to fuse into the single stereoscopic cyclopean view all normal people enjoy. Faced with the impossibility of fusing the vision of the two eyes, for whatever reason, the eye-brain system resorts to 'turning down' the response of one eye and so developing a one-eyed vision system. The 'turning down' of the sensitivity of the eye is concentrated at and around the fovea of the amblyopic eye, the resulting 'blind spot' concentrated around the fovea is called the scotoma. The amblyopic eye therefore has a 'blind spot' which can be very large, several degrees wide and tall, surrounded by a more or less normal peripheral vision.

When the amblyopic eye is used alone, the naive subject is unaware of the blind spot, because the eye swivels so as to obtain the best image it can from the best parts of the remaining peripheral vision. Thus when an eye care practitioner measures the optical acuity of an amblyopic eye it may well be a measure of the acuity of a portion of the peripheral vision of the amblyopic eye. In general it is likely not to be a measure of the remaining performance of the foveal portion of the retina, which will likely be effectively zero in an older subject. Seeing with the amblyopic eye alone is best with anomalous fixation, which is not something an eye care practitioner is likely to want to encourage.

When the amblyopic eye and the normal eye are used together, the vision experienced by the subject is as if he were seeing entirely out of the good eye; apart from some extreme peripheral vision of the amblyopic eye. An individual driving on the left of the road with an amblyopic right eye will be aware of the overtaking car seen in the peripheral vision of the amblyopic eye as if it had been seen by the good eye, even though the good eye cannot possibly have seen it. However, in general it is very difficult to comprehend what, if anything, is being 'seen' through the amblyopic eye when the two eyes are being used binocularly.

Amblyopia, and the associated loss of depth perception, is also known to affect a subject's interpersonal relationships and in particular how they relate to others.

In view of this, diagnosis and treatment of amblyopia is in the subject's best interests. Traditional methods of treatment of amblyopia include surgery and/or patching, and are typically limited to being performed on young children, such as pre-teens. In this regard, it is typically thought that once a subject is above about 12 or 13 years of age, the eye and brain 'seeing' system has sufficiently matured that any further treatment will no longer be effective.

Typically amblyopia is caused by either a muscle misalignment in a subject's eye, or by differently calibrated optical systems in each eye, for example, with the result that one eye dominates. Therefore, surgery in subjects with amblyopia can involve attempting to properly align a subject's eye by correcting the controlling muscles. However, eye surgery is an invasive procedure with a relatively low success rate, and in some instances, a subject may still need to undergo some type of vision training post-operatively in order to 'learn' to use both eyes binocularly.

Patching is traditionally utilised for vision training of children with amblyopia. In particular, the method typically involves obscuring the entire field of view of the dominant eye using a patch, such that the subject is forced to rely solely on the non-dominant eye. However, patching has also proven to have poor outcomes, with children responding poorly to having to wear a patch for prolonged periods, often resulting in the child being ostracised by their peers. In addition, patching has limited success in training the subject to overcome their amblyopia.

SUMMARY OF THE PRESENT INVENTION

The present invention seeks to ameliorate one or more of the problems associated with the prior art.

In a first broad form the present invention seeks to provide an apparatus for use in visual training of a subject, the apparatus including an at least partially opaque elongate occluder for at least partially occluding a substantially laterally oriented area of a field of view of a first eye so as to define an occluded area and a non-occluded area, and, wherein in use the occluded area moves relative to the field of view, and the subject:

a) views at least one target that extends into the occluded area using both eyes so that the subject perceives an image of the target, the image in the non-occluded area being at least partially based on signals from the first eye and the image in the occluded area being at least partially based on signals from a second eye; and, b) ensures the target is at least partially aligned in the occluded and non-occluded areas.

Typically the apparatus includes a support.

Typically the apparatus is for treating amblyopia.

Typically the occluder defines any one of:

a) an at least partially opaque region; and, b) an at least partially opaque member.

Typically the apparatus includes:

a) one or more displays including a plurality of pixels;

b) each pixel is in any one of a first state and a second state, wherein in the first state the pixel is at least partially opaque, and in the second state the pixel is substantially transparent; and, c) wherein the opaque region is defined by one or more pixels in the first state.

Typically the apparatus includes selectively controlling the plurality of pixels thereby to selectively control the opaque region.

Typically each display includes:

a) one or more display elements supported in series across at least part of the field of view;

b) each display element includes a plurality of pixel elements; and, c) wherein each pixel includes a pixel element from each of the one or more display elements.

Typically the support includes any one of:
a) a pair of spectacles;
b) a hat; and,
c) a head band.

Typically the apparatus includes a safety bather mounted between the opaque member and the eyes of the subject.

Typically the apparatus includes a switch that in use allows a user to toggle the apparatus between an operative and an inoperative state, wherein in the inoperative state the field of view is substantially not occluded.

Typically the apparatus including a controller for controlling a position of the opaque member relative to the first eye.

Typically the apparatus includes an electronic processing system, the processing system for:
a) determining a visual training procedure; and,
b) controlling the controller in accordance with the determined visual training procedure.

Typically, in use the apparatus moves the occluder in a direction substantially perpendicular relative to a lateral direction.

In a second broad form the present invention seeks to provide an apparatus for use in visual training of a subject, the apparatus being for at least partially occluding a substantially laterally oriented area of a field of view of a first eye so as to define an occluded area and a non-occluded area, and wherein, in use, the occluded area moves relative to the field of view, and the subject:
a) views at least one target that extends into the occluded area using both eyes so that the subject perceives an image of the target, the image in the non-occluded area being at least partially based on signals from the first eye and the image in the occluded area being at least partially based on signals from a second eye; and,
b) ensures the target is at least partially aligned in the occluded and non-occluded areas.

In a third broad form the present invention seeks to provide a method for use in visual training of a subject, the method including:
a) at least partially occluding an area of a field of view of a first eye so as to define an occluded area and a non-occluded area;
b) moving the occluded area relative to the field of view;
c) viewing at least one target that extends into the occluded area using both eyes so that the subject perceives an image of the target, the image in the non-occluded area being at least partially based on signals from the first eye and the image in the occluded area being at least partially based on signals from a second eye; and,
d) ensuring the target is at least partially aligned in the occluded and non-occluded areas.

Typically the method is for treating amblyopia in the second eye.

Typically the method includes relatively moving the target and the field of view of the subject.

Typically relatively moving the target and the field of view is achieved by any one of:
a) movement of the subject;
b) movement of part of the subject;
c) movement of the subject's eyes; and,
d) movement of the target.

Typically, the method includes moving an occluded area in a direction substantially perpendicular relative to a lateral direction.

Typically moving the occluded area is achieved by any one of:
a) movement of the subject; and,
b) movement of the occluded area relative to the first eye.

Typically the method includes oscillating the occluded area substantially within the field of view.

Typically a period of oscillation includes any one or more of:
a) between 0.01 Hz and 5 Hz;
b) between 0.1 Hz and 2 Hz; and,
c) between 0.5 Hz and 1.5 Hz.

Typically the method includes moving the occluded area substantially parallel to any one of:
a) a coronal plane of the subject;
b) a transverse plane of the subject; and,
c) an oblique plane of the subject.

Typically the method includes moving the occluded area in any one of regularly and irregularly.

Typically the method includes moving an at least partially opaque occluder that defines the occluded area.

Typically the occluder defines an at least partially opaque region.

Typically the target is an elongate target.

Typically the occluded area extends perpendicularly to the target.

Typically the occluded area is shaped substantially according to any one of:
a) a circle;
b) a square;
c) a rectangle;
d) an elongate rectangle; and,
e) an ellipse.

Typically the occluded area includes graduated edges.

In a fourth broad form the present invention seeks to provide a method for treating amblyopia in a second eye of a subject, the method including:
a) at least partially occluding an area of a field of view of a first eye so as to define an occluded area and a non-occluded area;
b) moving the occluded area relative to the field of view;
c) viewing at least one target that extends into the occluded area using both eyes so that the subject perceives an image of the target, the image in the non-occluded area being at least partially based on signals from the first eye and the image in the occluded area being at least partially based on signals from the second eye; and,
d) ensuring the target is at least partially aligned in the occluded and non-occluded areas.

In a fifth broad form the present invention seeks to provide an apparatus for use in visual training of a subject, the apparatus including an at least partially opaque occluder for at least partially occluding an area of a field of view of an eye of the subject, wherein in use the occluder moves in a direction substantially perpendicular relative to a lateral direction of the eye.

Typically, the occluder is elongate and oriented in the lateral direction.

BRIEF DESCRIPTION OF THE DRAWINGS

An example of the present invention will now be described with reference to the accompanying drawings, in which:—

FIG. 3A is a schematic diagram of an example of a field of view of a second eye;

FIG. 3B is a schematic diagram of an example of a field of view of a first eye included occluded and non-occluded areas;

FIG. 3C is a schematic diagram of an example of an image of a target based on signals from the first eye and second eye;

DETAILED DESCRIPTION OF THE PREFERRED EMBODIMENTS

An example of a method and apparatus for use in visual training will now be described with reference to FIGS. 1 to 3.

In the following, the term 'subject' is used to refer to a person who is using the apparatus 100 for the purpose of visual training and in one particular example, for the purpose of treating an eye condition, such as squints or amblyopia. The term 'user' is used to include the subject or another user, such as a parent, a carer, a guardian, an eye care practitioner, or the like. The term 'eye care practitioner' refers to any person permitted to practice eye care in various jurisdictions such as an orthoptist, optometrist, ophthalmologist or the like. In addition, the term 'target' is used to include any feature, object or item that can be observed visually.

Figure 2:
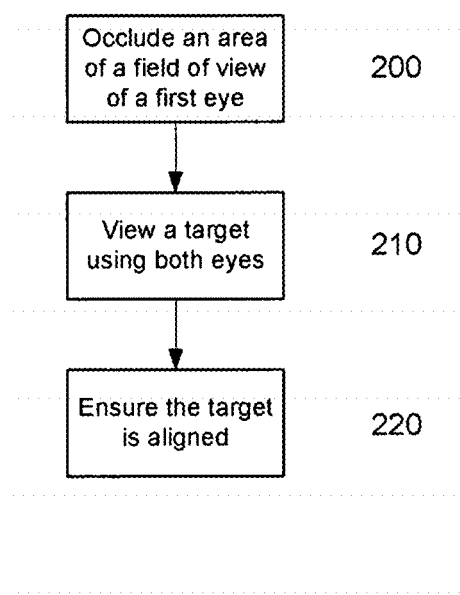
FIG. 2 is a flowchart of an example of a method of visual training.

In this example, the apparatus 100 includes an at least partially opaque occluder 110, and in one example an occluding bar, which at step 200 of FIG. 2 is used to at least partially occlude an area of a field of view $FOV_F$ of a first eye F so as to define an occluded area O and a non-occluded area NO. Optionally the apparatus 100 may include a support, and this is discussed in more detail below.

At step 210, the subject views at least one target that extends into the occluded area using both eyes, as will now be described with reference to FIGS. 3A to 3C, so that the subject perceives an image I of the target $T_F$, $T_S$, the image in the non-occluded area NO being at least partially based on signals from the first eye and the image in the occluded area O being at least partially based on signals from a second eye. In particular, FIG. 3A shows an example of a field of view $FOV_S$ of a second eye S based on signals from the second eye S, and which includes a target $T_S$, and FIG. 3B shows an example of a field of view $FOV_F$ of a first eye F based on signals from the first eye F, and including the same target $T_F$.

At step 220, the subject ensures, or attempts to ensure that, the target $T_F$, $T_S$ is at least partially aligned in the occluded O and non-occluded areas NO.

Thus, in the example of FIG. 3C, the target $T_S$ in the occluded area O and the target $T_F$ in the non-occluded area NO are not aligned, and accordingly, the subject attempts to adjust their eyes to ensure they are aligned. This can be achieved by any suitable technique appropriate to the subject, for example, by mental rumination and reminding the subject of the nature of the target, or alternatively can be achieved by realigning the focus of the eyes, for example using the muscles in the eye.

FIG. 3C is for demonstrative purposes only, and indeed some subjects may perceive the image I of the target as already aligned, or with more pronounced misalignment, only slight misalignment, or the like.

In addition, a subject may perceive some blurring, or darkening at an edge of the occluded area, and this may be known as a penumbra, or a penumbra region P, as shown in FIG. 3C. However, this is not essential, and a subject may perceive an image without the penumbra, or with larger or smaller penumbra, or the like.

A myriad of variations of the respective fields of view are possible based on the signals from the respective eyes, for example, in some subjects with eye conditions such as amblyopia a scotoma may exist which occludes at least a portion of the field of view, hence these Figures are to aid explanation only.

The abovementioned apparatus 100 offers numerous advantages.

For example, the apparatus 100 may be used in the treatment of amblyopia, or lazy eye. In this regard, the first eye would typically include the dominant eye, whilst the second eye would include the amblyopic, or lazy, eye. Therefore, the second eye could include the left eye or the right eye. In addition, the apparatus 100 may be used in the treatment of other appropriate eye defects, such as squints.

In particular, a subject may only be required to repeatedly perform the method, or utilise the apparatus 100, for one or more relatively short periods of time per day, for example each period may be typically between 1 and 30 minutes, more typically between 1 and 15 minutes, and/or more typically about 2 minutes. In this respect, the subject may begin to experience anything from at least partial stereoscopic peripheral vision to full stereoscopic vision typically after 1 to 30 sessions, more typically 5 to 20 sessions, and more typically about 14 sessions.

In other examples, the subject may repeatedly perform the method, or utilise the apparatus 100, for more prolonged periods, such as for one or more hours. Each of these periods may be performed as appropriate, and in some instances every day, on alternate days, one or more days per week, or the like.

In this context, it has been shown that utilising the apparatus 100 can aid in at least partially restoring stereoscopic peripheral vision or full stereoscopic vision in both younger subjects, as well as older subjects who have traditionally been thought beyond treatment. In particular, as the subject views one or more targets that extends into the occluded area using both eyes, the subject's brain is forced to consider signals from the second eye in order to perceive the image in the occluded area O while the subject is ensuring, or attempting to ensure that, the target $T_F$, $T_S$ is at least partially aligned in the occluded O and non-occluded areas NO. Thus, the subject's brain learns not to discount signals from the second eye, and hence allows signals from the second eye to be increasingly used in order to improve at least peripheral stereoscopic vision.

In addition, the method is non-invasive, and as it may only require performing the method for shorter intervals during the day, can be performed in private. Therefore, this significantly reduces the risk of subjects being ostracised and/or excluded by peers due, for example, to the presence of the apparatus 100.

The apparatus 100 and method described above have also been shown to be particularly advantageous in improving bi-ocular vision of the subject. Additionally it has been shown that the described method and apparatus 100 are advantageous in improving wide-angle stereopsis in a subject.

Thus, the above described method and apparatus 100 is particularly advantageous, and has been shown to be superior to other techniques, for example, techniques utilising computer screens for displaying 'three-dimensional' objects. Such techniques merely simulate three-dimensional objects, whereas in reality the simulated objects are merely located at the same distances and hence same 'eye-pointing' distance. Thus, these techniques have questionable application in the real world in which objects are in reality at different distances relative to the subject's eyes, and thus require different 'eye-pointing' distances. Thus, the method and apparatus 100 described here offers is beneficial in providing real-world exposure to targets at variable distances, and using variable eye-pointing distances, which directly leads to vision improvements in real world situations.

In addition, subjects who suffer from vision difficulties, such as amblyopia, are know to rely on 'secondary cues' in order to improve their depth perception of objects in the real world. Secondary vision cues can include shadows, and other pictorial cues. However, it is not typically possible to rely on secondary cues in a simulated environment, such as on a computer screen, thus the above described method and apparatus 100 offers a further benefit in a providing a training environment including real-world secondary cues.

A number of further features will now be described.

Figure 1A:
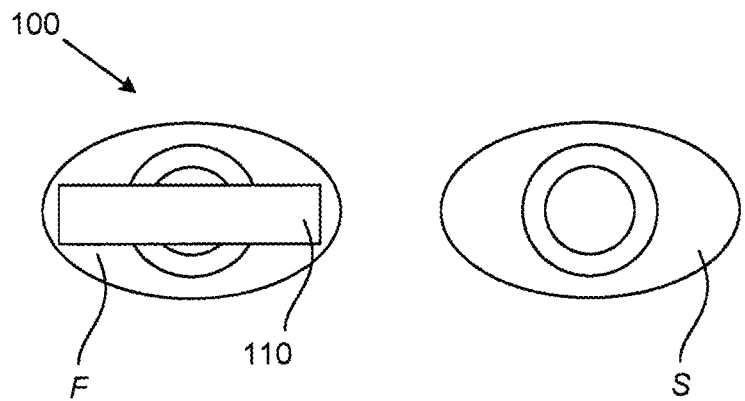
FIG. 1A is a schematic diagram of a front view of a first example of an apparatus for use in visual training.
Figure 1B:
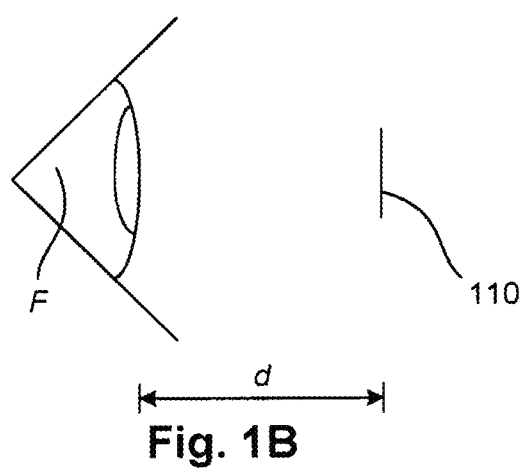
FIG. 1B is a schematic diagram of a side view of the apparatus of FIG. 1A.

In one example, the apparatus 100 includes an elongate occluder 110 for at least partially occluding a substantially laterally oriented area of the field of view, for example, as shown in FIGS. 1 and 3B. Thus the apparatus 100 occludes a substantially laterally oriented area of the field of view, which may be beneficial for subjects with pointing errors where their two eyes do not point in an appropriate direction across a substantially horizontal plane or lateral eye direction, a misalignment which may lead to a condition referred to as 'squint', and this will be discussed further below. However, whilst amblyopia may be caused by squints, squints do not necessarily cause amblyopia instantly, and it may be possible to correct a squint using the apparatus 100 before the subject experiences amblyopia.

Additionally or alternatively, the method and/or apparatus 100 in use includes moving the occluder 110 and/or occluded area in a direction substantially perpendicular relative to a lateral direction. In this regard, the lateral direction refers to a lateral direction of the subject's second eye.

Thus, in one example the apparatus includes an at least partially opaque occluder for at least partially occluding an area of a field of view of an eye of the subject, wherein in use the occluder moves in a direction substantially perpendicular relative to a lateral direction of the eye. Additionally, the occluder may optionally be elongate and oriented in the lateral direction.

The eyes of a subject are displaced sideways in a substantially horizontal plane by a distance of typically about 60 to 70 mm relative to the other. Whilst, due to the different positioning of the eyes, the eyes do not experience the 'same' view of the world, typically discrepancies in the two views are not perceived by the subject.

'Stereopsis' arises due to the differences experienced in the relative views of the eyes. In the example of a nearby object, the eyes of a subject typically move through different lateral angles in order to obtain respective images of the object on corresponding places on the respective retinas. In this regard, other objects which are either closer or more distant from the eye than the object being viewed will now no longer line up, however these discrepancies will be accommodated for in the 'image processing' which occurs in the brain.

Thus, in order to appropriately view a particular object, a subject's eyes point toward the object, which typically requires at least some lateral eye movement, and the subject's brain subsequently processes the respective views in order to superimpose them, correct for any discrepancies and form a three-dimensional view. These adjustments to the perceived position of the different component parts of the object typically require the evaluation of tiny angular differences in direction of the views within the two eyes.

For most people the angular errors introduced by a tiny squint and/or misalignment of the eyes, can be enough to compromise the process of stereoscopy, leading to at least partial inaccuracies. In turn this may lead to amblyopia, however other causes of amblyopia are possible, for example, a refractive error in one eye.

Thus, misalignment problems with the eyes of a subject typically arise as a result of pointing errors in eyes relative to a substantially horizontal plane and/or lateral eye direction. Thus, the abovementioned arrangement, in which the occluder 110 is substantially laterally oriented, with the occluder 110 in being moved in a direction substantially perpendicular relative to the lateral direction, is particularly beneficial in the treatment of this type of misalignment.

However, some subjects may additionally or alternatively experience misalignment in substantially the vertical plane, and thus would benefit from different positioning and movement of the occluder 110, as discussed below. It is also possible that one eye movement of a subject is not in a plane parallel to the plane of movement of the other, and as such, treatment of this may additionally or alternatively require an oblique movement and/or oblique orientation of the occluder 110.

In any one of the above examples, the occluder 110 is an at least partially opaque member, however this is not essential and in other examples the occluder 100 may be an at least partially opaque region, and this will be discussed further below.

As discussed above, the occluder 110 in the example of FIG. 1 is an elongate rectangle which is substantially parallel to the transverse plane of the subject, and substantially perpendicular to the medial plane of the subject. In this regard, the elongate rectangle is also oriented in the lateral direction. However, this is not essential and in other examples the occluder 110 is parallel to, or otherwise oriented with respect to, the medial plane, for example, perpendicular to the lateral direction, or in any other suitable orientation. Additionally, the occluder 110 may be moved in any suitable direction, such as in a lateral direction, or the like. Further, the occluder 110 may define any suitable shape with respect to the field of view of the first eye F, including any one of a circle, a square, a rectangle, an ellipse, a regular shape, and irregular shape, or the like.

Additionally, the occluder 110 may be any suitable size relative to the field of view of the first eye F. In this regard, the relative size of the occluder 110 in respect of the field of view, will be dependent upon the dimensions of the occluder 110 and the distance of the occluder 110 from the first eye F of the subject. In one example, the occluder 110 is typically positioned between 10 mm and 100 mm from the first eye of the subject, more typically between 10 mm and 30 mm, and more typically about 20 mm from the first eye. In addition, the occluder 110 typically includes has a width of between 3 mm and 50 mm, more typically the width is between 5 mm and 15 mm, and more typically about 10 mm. However this is not intended to be limiting and it will be appreciated that any suitable size and/or position could be used.

Furthermore, in this example the occluder 110 uniformly occludes an area of the field of view of the first eye F, however this is also not essential. In some examples the occluder 110 defines an occluded area including graduated edges, stepped changes in transparency, and/or include regular or irregular transparency.

Also in the above example, the target $T_F$, $T_S$ is an elongate target, and the occluder 110 is substantially perpendicular to the target. Thus, in a preferred arrangement the target(s) may be tall and substantially vertical. However this is not essential and in other examples the target may be any suitable shape and/or orientation, dependent upon, for example, the shape of the occluded area O. For example, the target(s) may be substantially horizontal, and/or oblique, or the like. In addition, the occluder 110 may be oriented in any suitable manner in respect of the target $T_F$, $T_S$.

In further examples, the subject may view more than one target, for example by viewing a number of different targets at different times. Whilst each of the targets may be at a similar distance, more typically different targets are provided at different distances to exercise the visual system for a range of different convergence angles. In this respect, a convergence angle corresponds to the angle between respective visual axes of the first and second eye, where a visual axis corresponds to an imaginary line passing from the viewed target to the fovea centralis. For example, targets at a greater distance, when viewed, will result in a smaller convergence angle between respective visual axes of the first and second eyes than targets at a closer distance. Hence, by viewing different targets at different distances, and thus using a range of different convergence angles, the subject's brain learns not to discount signals from the second eye at a range of convergence angles.

In this regard, each of the targets may be provided at any suitable distance from the subject including, for example, any distance within the range extending from less than 1 metre to more than 10 m, and more typically to the visible horizon. More typically, the target(s) may be at a distance in the range from 300 mm to several metres from the subject, and occasionally to the horizon. Furthermore, the different distances of the targets may include a large variation, for example, at least one of the targets may be at a distance of less than 1 m from the subject and at least one of the targets may be near the horizon. However, this is not essential and in other embodiments more than one target may be provided at a largely similar distances from the subject. Alternatively, a single target may be provided at any of the suitable distances provided in the ranges discussed above.

In other examples, the method, and/or the apparatus 100 in use, includes relatively moving the target and the field of view of the subject, an effect which may be referred to as 'streaming'. This may be achieved in any suitable manner, such as by movement of the subject and/or movement of part of the subject and/or movement of the subject's eyes, which in some instances has shown to be particularly beneficial. For example, the subject may use the apparatus 100 while walking, running, moving in a vehicle, or the like, and/or by movement of the subject's head, upper body, eyes, or the like. In this regard, the subject may directly view one or more of the targets, or in other examples, viewing may be via the subject's peripheral vision.

Additionally or alternatively, relatively moving the target and the field of view may be achieved by movement of the target(s). For example, the subject may use the apparatus 100 while substantially stationary in a crowded space, such that targets about the subject are moving.

In some instances, subjects suffering from amblyopia may experience 'anomalous correspondence', where in order to view an object the lazy eye may physically deviate from the visual direction of the normal eye. It has been shown that performing the method, or using the apparatus, as described herein while 'streaming' of targets occurs is beneficial in reducing anomalous correspondence.

In a further example, the number and density of targets may be varied. For example, it may be beneficial in some instances to increase the number and density of targets which the subject views when performing the method and/or using the apparatus. This has been found to be particularly advantageous in treating amblyopia, for example, when targets are cluttered. Optionally, streaming of cluttered targets may also be used.

In some embodiments it may be desirable to repeat at least part of the method of visual training. For example, a subject may perform the method a plurality of times in succession, or periodically or sporadically over an extended period of time.

In a further example, the method includes moving the occluded area O relative to the field of view $FOV_F$. This may be achieved through either movement of the subject, or movement of the occluded area O relative to the first eye F. In an example of the former, the occluded area O is moved relative to the field of view $FOV_F$ by moving the head of the subject, for example by nodding or shaking or any other movement of the head of the subject. Alternatively, the eyes of the subject may be moved relative to the occluder 110, thus effecting a relative movement of the occluded area O with respect to the field of view $FOV_F$.

Movement of the occluded area O relative to the first eye F may also be achieved in any suitable manner, such as movement of the occluder 110. In this regard, the occluder 110 may be moved in any suitable direction relative to the first eye F, and this can also be achieved in any suitable manner, as will be discussed further below.

In one example, the method includes oscillating the occluded area O substantially within the field of view $FOV_F$. In this respect, a period of the oscillation is typically included within the range of 0.05 Hz to 5 Hz, more typically within the range of 0.1 Hz and 2 Hz, and more typically within the range of 0.5 Hz and 1.5 Hz.

In addition, the occluded area O may be moved in any suitable manner, such as in a direction substantially perpendicular relative to a lateral direction, as discussed above, or substantially parallel to a coronal plane of the subject, a transverse plane of the subject, and/or an oblique plane of the subject. Furthermore, the movement may be regular or irregular depending upon the subject and type of visual training.

For example, some subjects have pointing errors where their eyes do not point in appropriate directions relative to the horizontal plane, for example, one eye pointing high, the other eye pointing relatively lower. Such subjects may benefit from an occluded area O oriented perpendicular to the lateral direction and moved and/or oscillated in the lateral direction.

In some examples, the apparatus 100 may be prescribed by, or used in, the presence of an eye care practitioner. In this respect, the eye care practitioner may wish to assess the health, movement, or the like, of the first and/or second eye prior to, during, or following visual training. Thus, it will be appreciated that the eye care practitioner may assess the first and/or second eye using any one or more optometry devices, including lenses, prisms, cameras, and the like, while the subject is using the apparatus 100. However, this feature is not essential.

Figure 4A:
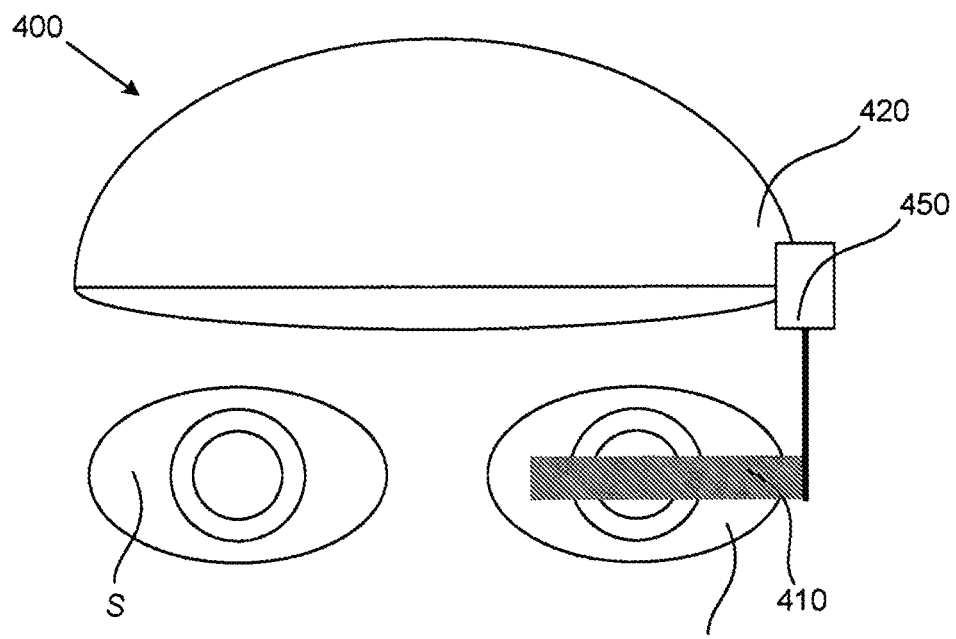
FIG. 4A is a schematic diagram of a front view of a second example of an apparatus for use in visual training.
Figure 4B:
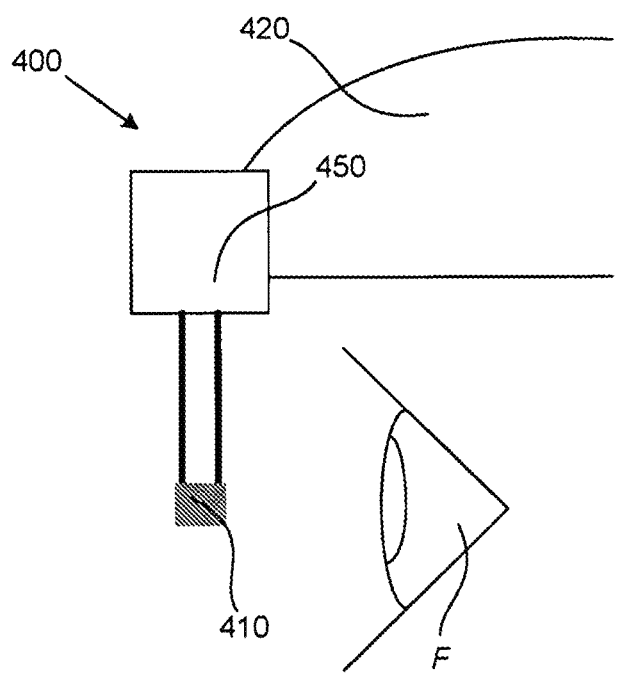
FIG. 4B is a schematic diagram of a side view of the apparatus of FIG. 4A.

A second example of an apparatus for use in visual training is shown in FIGS. 4A and 4B. Features similar to those of the example described above have been assigned correspondingly similar reference numerals.

In this example, the apparatus 400 includes a support 420 such as a hat similar to a hardhat or helmet. However, this is not essential and any suitable type of support may be used including a pair of spectacles, a soft hat, a cap, a head band, a neck support, a hand-held support, or the like. An at least partially opaque member 410 is coupled to an actuator which in turn is supported on the support 420, where operation of the actuator is controlled by a controller 450.

The controller 450 controls a position of the opaque member 410 relative to the first eye F. The controller 450 may be any suitable controller 450, for example, a processor, such as a microprocessor, a programmable logic controller (PLC), a field programmable gate array (FPGA) or any other electronic or mechanical device, system or arrangement capable of interacting with the opaque member 410.

In one example, the actuator may include a stepper motor and linear actuator, such that the controller 450 controls the stepper motor which in turn controls the linear actuator, upon which is mounted the opaque member 410. In this regard, in use, the linear actuator causes the opaque member 410 to move in a direction parallel to, perpendicular to, or oblique with respect to a medial axis of the subject, or in any other suitable direction as discussed above.

However, this is not compulsory and in some embodiments the actuator may include a motor and rotary actuator, such that the opaque member 410 is rotated about an axis. In some examples an actuator is not required, and this will be discussed further below.

In some embodiments, the apparatus 400 further includes a safety barrier (not shown) mounted between the opaque member and an eye or both eyes of the subject. The safety barrier may be any suitable barrier, for example, the barrier will typically be substantially transparent, and may include safety glasses, Perspex, safety glass, spectacles, an at least semi-rigid material mounted to the support, or the like. Spectacles may be used in addition to, or as an alternative to, the safety barrier, however this is not essential.

Figure 5A:
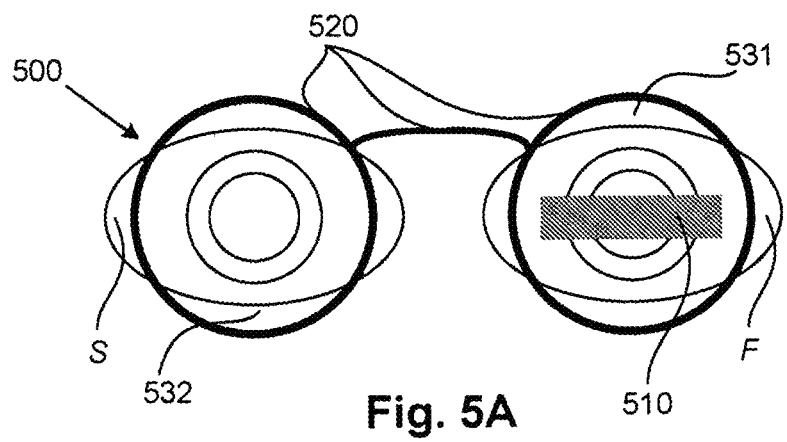
FIG. 5A is a schematic diagram of a front view of a third example of an apparatus for use in visual training.
Figure 5B:
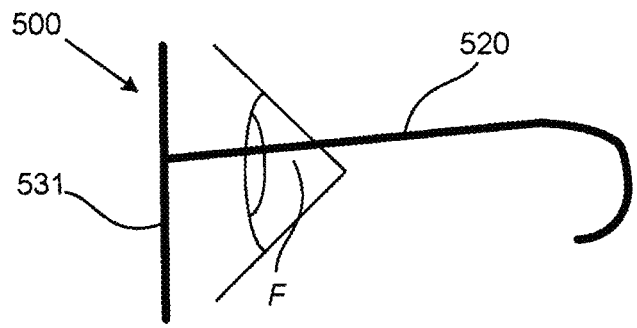
FIG. 5B is a schematic diagram of a side view of the apparatus of FIG. 5A.
Figure 5C:
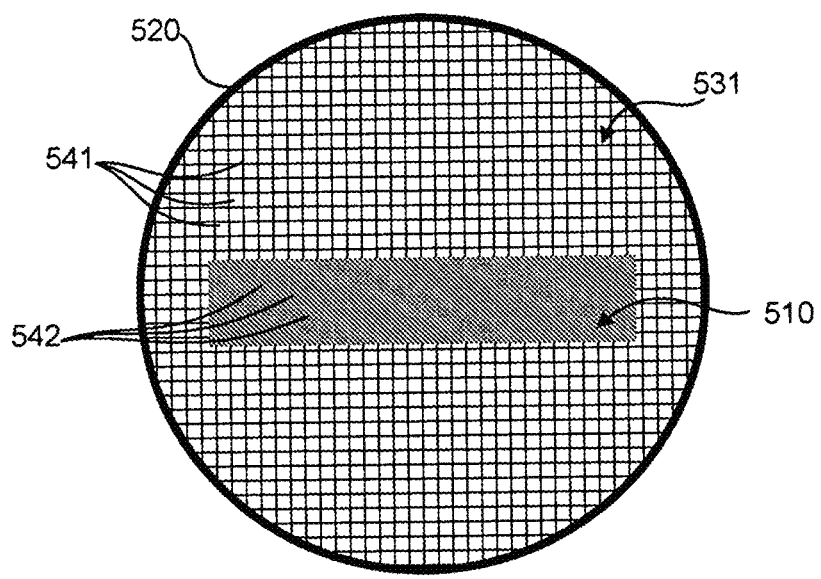
FIG. 5C is a schematic diagram of a front view of a display of the apparatus of FIG. 5A.
Figure 6A:
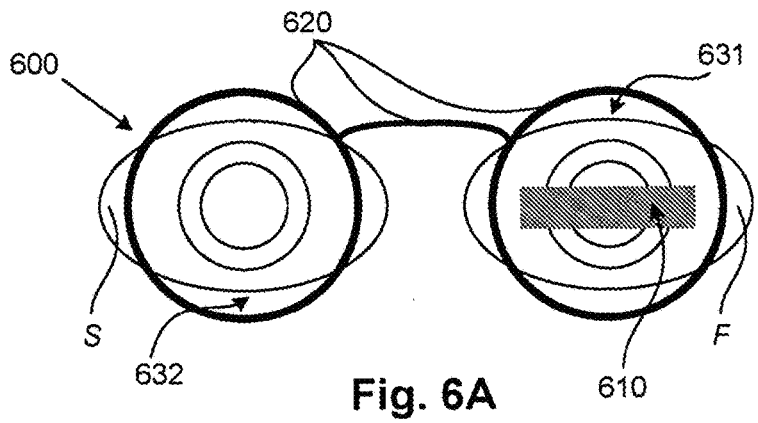
FIG. 6A is a schematic diagram of a front view of a fourth example of an apparatus for use in visual training.
Figure 6B:
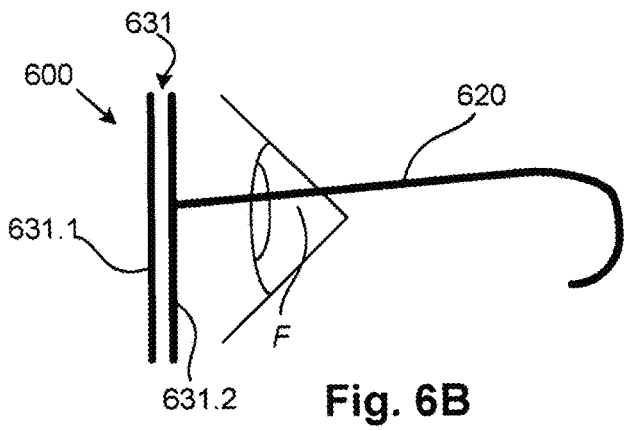
FIG. 6B is a schematic diagram of a side view of the apparatus of FIG. 6A.
Figures 6C, 6D, 6E:
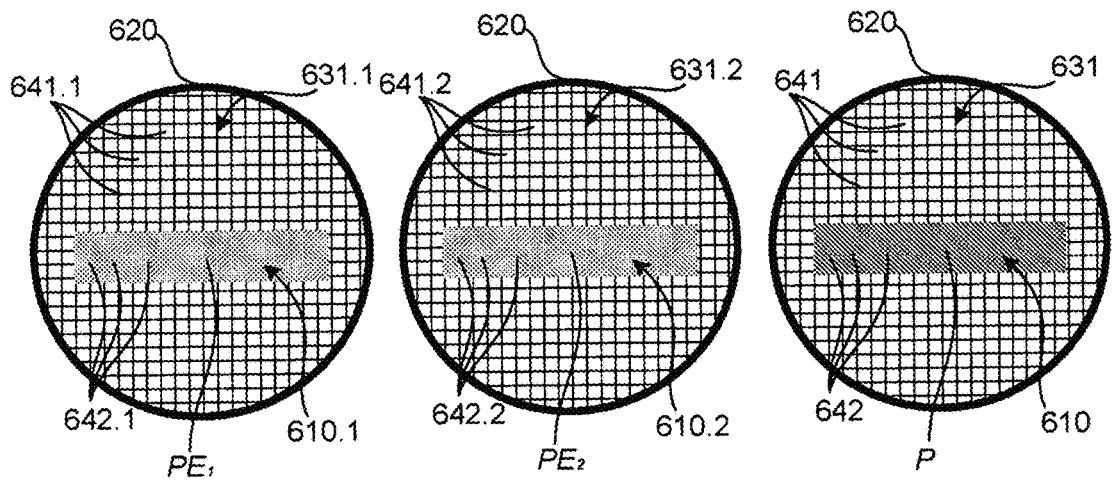
FIG. 6C is a schematic diagram of a front view of a first display element of the apparatus of FIG. 6A.
FIG. 6D is a schematic diagram of a front view of a second display element of the apparatus of FIG. 6A.
FIG. 6E is a schematic diagram of a front view of a display of the apparatus of FIG. 6A, including the display elements of the examples in FIGS. 6C and 6D.

A third example of an apparatus for use in visual training is shown in FIGS. 5A, 5B, and 5C. Features similar to those of the examples described above have been assigned correspondingly similar reference numerals.

In this example, the apparatus 500 includes a support 520, which is a pair of spectacles, and two displays 531, 532. However, it will be appreciated that any suitable number of displays may be used, for example a single display across either one eye, such as the first eye F, or both eyes. One display is used to display an occluder, which in this example is an at least partially opaque region 510 of the display.

In particular, the displays 531, 532 include a plurality of pixels, where each pixel is in a first state 542, or a second state 541. In this respect, in the first state 542 the pixel is at least partially opaque and in the second state 541 the pixel is substantially transparent. Accordingly, the opaque region 510 is defined by one or more pixels in the first state.

The apparatus 500 may include a controller (not shown), that selectively controls the plurality of pixels in one or more displays 531, 532 to thereby control the opaque region 510. The controller may be any suitable controller such as an electronic processing device, microprocessor, microchip processor, logic gate configuration, firmware optionally associated with implementing logic such as an FPGA (Field Programmable Gate Array), or any other electronic device, system or arrangement capable of interacting with the displays 531, 532.

In one example, the displays 531, 532 include transparent liquid crystal display (LCD), or transparent transmission LCD, screens in which pixels can be darkened and made opaque. However, this is not essential and any suitable displays 531, 532 may be used which include a plurality of pixels 540 capable of being in the first or second state. For example, a transparent light emitting diode (LED) display, a transparent organic light emitting diode (OLED) display, or the like.

In addition, the apparatus 500 typically includes a power supply, or is coupled to a power supply, in any suitable manner. In one example, the power supply includes a battery, such as a battery suitable for a hearing-aid, which may be mounted to, or provided within the support 520. Alternatively, the apparatus 500 may be coupled to an external power supply, such as mains power, an external battery, or the like, via any suitable coupling, such as a cable.

In use, typically the opaque region 510 is provided in the field of view of a first eye. In this respect, the controller controls the plurality of pixels in one or more displays 531, 532 to thereby selectively provide one or more pixels 540 in a first state 542 to define the opaque region 510. This may be achieved in any suitable manner depending upon the nature of the displays 531, 532. For example, it will be appreciated that methods of selectively controlling the transparency of pixels in transparent LCD, LED or OLED displays are known and therefore will not be discussed further here.

The pixels 540 in the first state 542 thus include an opacity such that light incident on a first side of the pixels 540 is reduced in intensity upon transmission to a second side of the pixels 540. In some examples, the opacity of all of the pixels 540 in the first state is substantially the same, however this is not essential and in other examples the opacities of some or all of the pixels 540 in the first state may be different.

In some examples, the apparatus 500 may also include a switch that in use allows a user to toggle the apparatus 500 between an operative and an inoperative state. In this respect, in the inoperative state of the field of view is substantially not occluded. For example, substantially all of the pixels in the displays 531, 532 may be in a second transparent state. In one example, the switch may be connected to the power supply, such that in a inoperative state the apparatus 500 is at least electrically decoupled from the power supply.

In addition, the switch may be positioned on the apparatus 500 in any suitable position, such as on support 520, for example, on the bridge of the support 520 between the displays 521, 532, or on one of the sides of the support 520. However, a switch is not essential, and in other alternatives the apparatus 500 may remain in an operative state, or toggle from an operative state to inoperative state by coupling and decoupling the power supply, respectively.

In other examples, the controller may be controlled by an electronic processing device, such as a processing system, and this will be discussed further below.

In another example, the display may include a composite mixture of materials. For example, the display may include a transparent material and one or more photochromic lenses, such that the opaque region largely corresponds to the photochromatic lenses and is visible upon introduction of the apparatus to light. This arrangement has the advantage that a power supply is not necessary. However, this feature is not necessary and the displays may be composed of any suitable material.

A fourth example of an apparatus for use in visual training is shown in FIGS. 6A to 6E. Features similar to those of the examples described above have been assigned correspondingly similar reference numerals.

In this example, an apparatus 600 for use in visual training of a subject includes a support 620, two displays 631, 632, and an at least partially opaque region 610 occluding an area of a field of view of a first eye F In particular, each display 631, 632 includes two display elements 631.1, 631.2 supported in series across at least part of the field of view of at least one eye. However, this number of display elements 631.1, 631.2 is not essential, and each display 631, 632 may include one or more display elements 631.1, 631.2.

In any event, each display element 631.1, 631.2 includes a plurality of pixel elements 641.1, 642.1, 641.2, 642.2, such that each pixel 640 corresponds to a pixel element 641.1, 642.1, 641.2, 642.2 from each of the one or more display elements 631.1, 631.2 in series. As discussed above, each pixel 640 is in a first state 642, or a second state 641. In this respect, in the first state 641 the pixel is at least partially opaque and in the second state 641 the pixel is substantially transparent. Accordingly, a pixel 640 is in the first state 642 if one or more of the corresponding pixel elements 642.1, 642.2 is in the first state, and a pixel 640 is in the second state 641 if all of the corresponding pixel elements 641.1, 641.2 is in the second state. The opaque region 610 is defined by one or more pixels in the first state.

For the purposes of explanation, reference will be made to a first pixel element $PE_1$ included on a first display element 631.1, a second pixel element $PE_2$ included on a second display element 631.2 and where the first and second pixel elements $PE_1$, $PE_2$ are in series, and a resultant pixel P which in this example is in the first state. In this explanatory example, the opacity of the resultant pixel P will depend upon the opacity of the first and second pixel elements $PE_1$, $PE_2$ in series. Therefore, in the event that light of an initial intensity passes through both pixel elements $PE_1$, $PE_2$ in series, and where both pixel elements $PE_1$, $PE_2$ are in the first state, a resultant intensity of light apparent at the resultant pixel P will be lower than had the initial intensity light merely passed through either of the first and second pixel elements $PE_1$, $PE_2$.

Thus increasing the number of display elements 631.1, 631.2 in series can increase the opacity of the resultant display 631 in the opaque region 610. In this respect, additional display elements 631.1, 631.2 may be used in order to increase the contrast between pixels 640 in the first state 642 and pixels 640 in the second state 641, and thus increase the contrast between the opaque region 610 and the remaining pixels in the display 631. Accordingly, this may ensure that when the subject perceives an image of the target, the image in the occluded area is based on more signals from a second eye than may be the case had the contrast between the opaque region 610 and the remaining pixels been lower. However, this is not essential and in other examples a pixel 642 may be in the first state where only one corresponding pixel element 642.1, 642.2 is in the first state.

When first and second pixel elements are in series, it is to be understood that the first pixel element substantially overlays the second pixel element relative to the field of view of the subject, and similarly for more than two pixel elements in series. Accordingly, when first and second display elements are in series, it is to be understood that the first display element substantially overlays the second display element relative to the field of view of the subject, and similarly for more than two display elements in series.

In this example, the support 620 includes a pair of spectacles, however this is not essential and in other examples the support 620 may include a hat, helmet, hardhat, headband or the like. As discussed above, the apparatus 600 may also optionally include a safety barrier.

Figure 7:
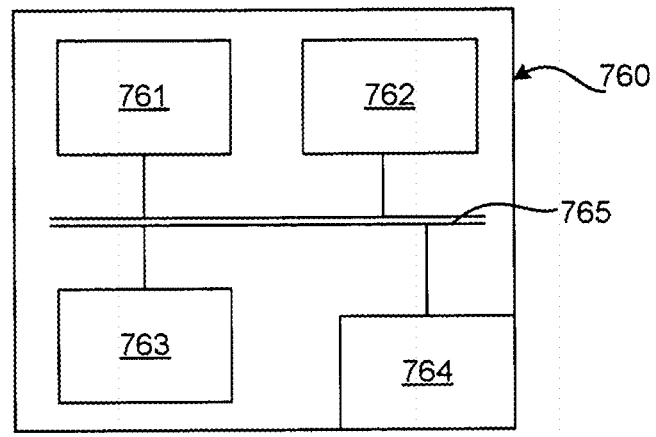
FIG. 7 is a schematic diagram of an example of a controller for use with the apparatus of any one of the FIGS. 1 and 4 to 6.

In some examples, an electronic processing device, such as a processing system, may control the controller 650, and an example of an electronic processing device 760 is shown in FIG. 7. The processing system 760 includes a processor 761, a memory 762, an input/output (I/O) device 763, such as a keyboard and display, and an external interface 764 coupled together via a bus 765. The external interface 764 is used for coupling the processing system 760 to peripheral devices, such as the controller 650, as well as to devices, such as communications networks, databases, other storage devices, or the like. Although a single external interface is shown, this is for the purpose of example only, and in practice multiple interfaces using various methods (e.g. Ethernet, serial, USB, wireless, mobile networks or the like) may be provided. It will also be appreciated that additional hardware components, may be incorporated into the processing system 760, depending on the particular implementation.

In use, the processor 761 executes instructions in the form of applications software stored in the memory 762 to allow control signals to be sent to the controller 650 to be executed, for example to control the display 610, and optionally to receive and interpret any signals from controller 650, for example to log when visual training is performed, as will be described in more detail below. Accordingly, for the purposes of the following description, it will be appreciated that actions performed by the processing system 760 are typically performed by the processor 761 under control of instructions stored in the memory 762, and this will not therefore be described in further detail below.

Accordingly, it will be appreciated that the processing system 760 may be formed from any suitably programmed processing system, such as a suitably programmed PC, Internet terminal, lap-top, hand-held PC, tablet PC, slate PC, iPad™, mobile phone, smart phone, PDA (Personal Data Assistant), or other communications device. Accordingly, the processor 761 can be any form of electronic processing device such as a microprocessor, microchip processor, logic gate configuration, firmware optionally associated with implementing logic such as an FPGA (Field Programmable Gate Array), or any other electronic device, system or arrangement capable of interacting with the controller 650 and optionally the display 610.

Figure 8:
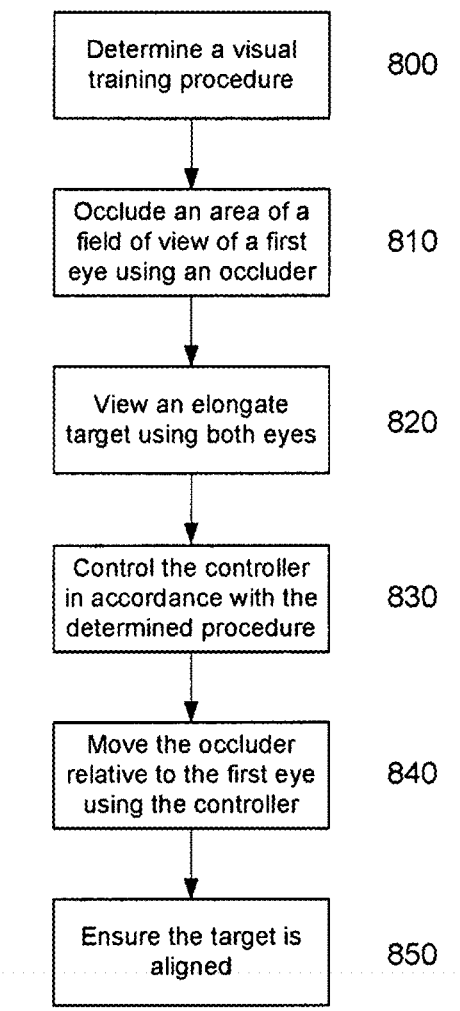
FIG. 8 is a flowchart of an example of a method of visual training using the controller of FIG. 7.

A second example of a method of visual training will now be described with reference to FIG. 8. At step 800, the processing system 760 determines a visual training procedure. This may be performed manually by the subject or another user such as an eye care practitioner, or automatically by the processing system 760. In this regard, the procedure may be determined based upon predetermined information such as the age of the subject, the number of times the subject has previously performed a visual training procedure, a presence, absence, or degree of a visual abnormality, such as amblyopia, in the subject, or the like.

At step 810 an area of a field of view of a first eye is at least partially occluded by an occluder so as to define an occluded area and a non-occluded area. In one example this is achieved using the processing system 760 which sends control signals to the controller, which in turn selectively controls pixels on a display in order to define an opaque region, as discussed above.

At step 820, the subject views at least one target that extends into the occluded area using both eyes so that the subject perceives an image of the target, the image in the non-occluded area being at least partially based on signals from the first eye and the image in the occluded area being at least partially based on signals from a second eye, as discussed above.

At step 830, the controller controls the occluder, or opaque region, in accordance with the determined visual training procedure. For example, the processing system 760 may continuously send control signals to the controller, or be continuously polled by the controller, during the visual training procedure. Alternatively, after step 800 the processing system 760 may transfer instructions corresponding to the entire visual training procedure to the controller, such that the controller interprets the instructions and generates control signals to control the occluder.

At step 840, the controller moves the occluder relative to the first eye, and this may be performed in any suitable manner such as discussed above.

At step 850, the subject ensures the target is at least partially aligned in the occluded and non-occluded areas. Optionally, this step may be performed while the occluder is moved, or when the occluder is stationary, or both.

In addition, in some examples steps 830 to 850 may be repeated, depending upon the determined visual training procedure, as discussed above.

Wider variations on the abovementioned arrangement are possible, including remote and/or cloud processing. For example, the processing system 760 may include a smartphone, or other computer system, which receives signals from the controller 650 indicating which visual training activities have been performed, transfers the signals to a remote server and/or cloud-based application for maintaining visual training logs for a particular subject. The smartphone may also receive visual training methods from the remote server or cloud application via signals which are then stored in memory 762 until the next time the subject performs visual training. For example, after performing a first variation of the visual training method a predetermined number of times, a second variation of the visual training method, such as a more difficult training activity, may be sent to the smartphone from the remove server. In this respect, the signals may be transferred remotely using any suitable method, such as using the Internet, USB, Ethernet, wireless, Bluetooth, mobile network, or the like.

Figure 9A:
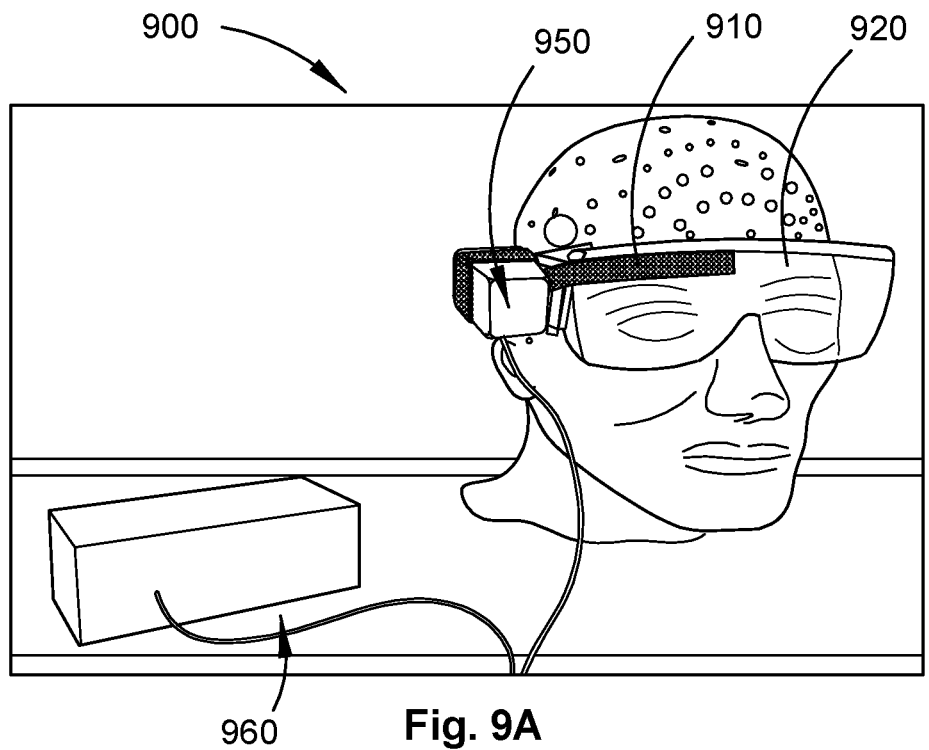
FIG. 9A is an image of a front view of a further example of an apparatus for use in visual training.
Figure 9B:
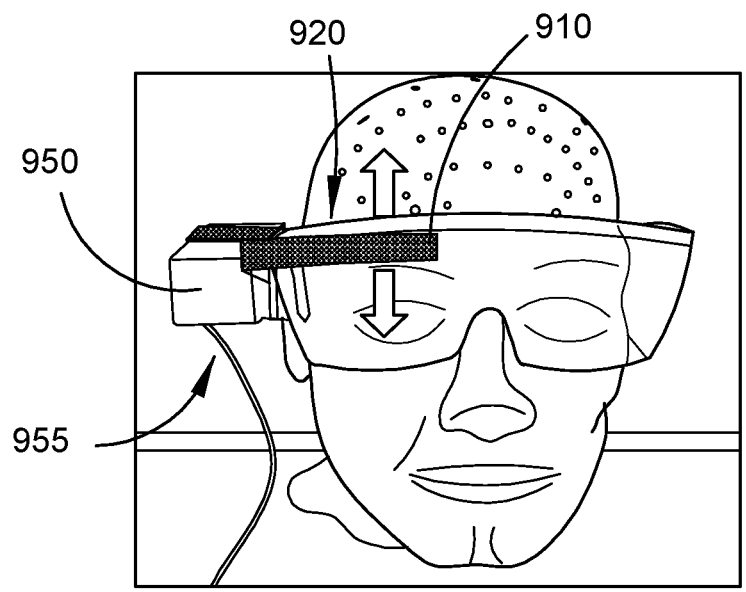
FIG. 9B is an image of a front view of the apparatus of FIG. 9B.

A further example of an apparatus for use in visual training is shown in FIGS. 9A and 9B. Features similar to those of the example described above have been assigned correspondingly similar reference numerals.

In this example, the apparatus 900 includes a pair of safety glasses 920 which acts as a support for supporting a geared DC motor 950 which actuates movement of the opaque member, which in this example is formed from an opaque strip 910. In this regard, any suitable motor 950 may be used, such as the motor sold under the trade name Solarbotics GM9 DC motor, and this will be described in more detail below.

In addition, the apparatus 900 includes an external power supply and motor controller 960 which is in electronic communication with the motor 950 via a wired connection 955. Thus the motor controller 960 in this examples controls the DC geared motor 950 to actuate substantially vertical movement of the laterally oriented opaque strip 910 in front of the subject's second eye, which in this example is the right eye, as shown in FIG. 9B.

Whilst the opaque strip 910 in this example is shown mounted in front of the right eye, the safety glasses 920 are configured to allow the motor 950 and strip 910 to be detached and reattached to the left side of the glasses 920. In this regard, the apparatus 900 may be configured for use with either eye, for example, for treating amblyopia in either eye of a subject.

Figure 10A:
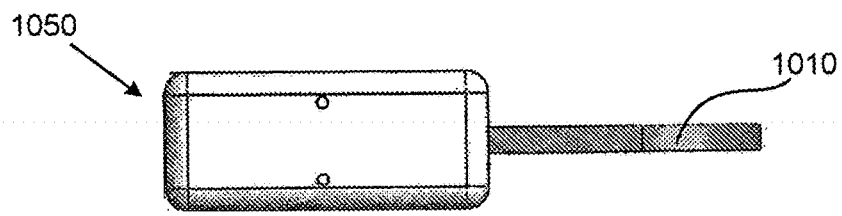
FIG. 10A is a schematic diagram of a side view of a further example of a motor and occluder of an apparatus for use in visual training.
Figure 10B:
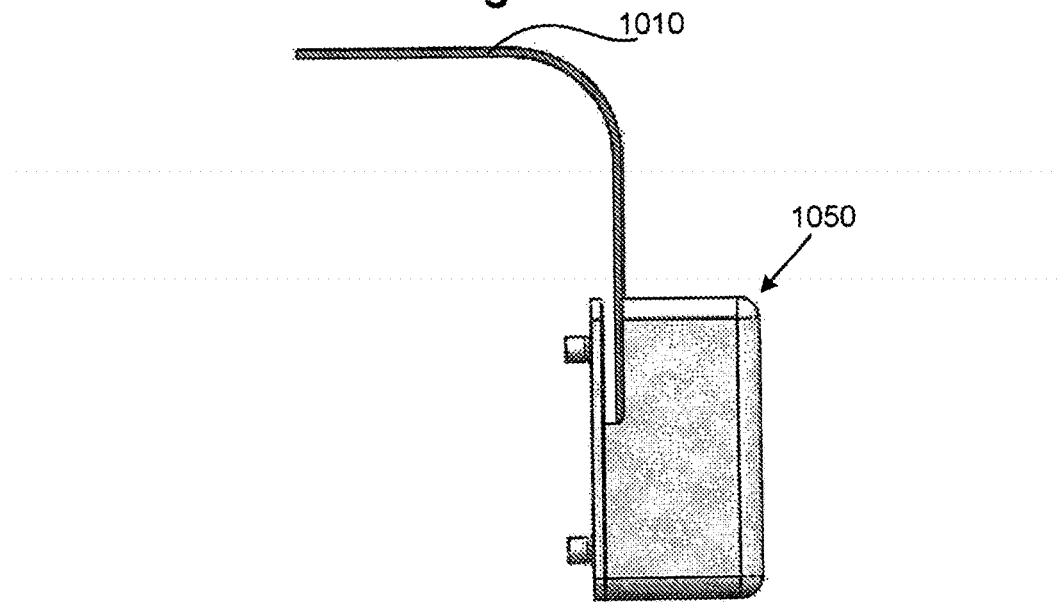
FIG. 10B is a schematic diagram of a top view of the motor and the occluder of FIG. 10A.
Figure 10C:
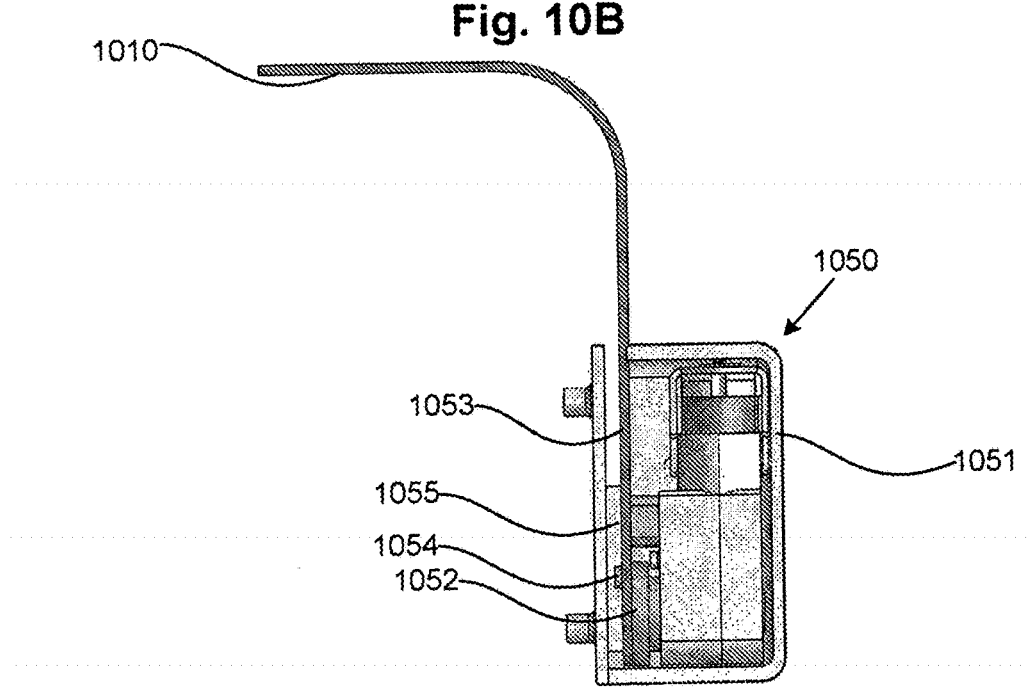
FIG. 10C is a schematic diagram of an internal view of the motor and the occluder of FIG. 10A.

An example of a geared DC motor for use in any of the above described apparatus is shown in FIGS. 10A to 10C. Features similar to those of the example described above have been assigned correspondingly similar reference numerals.

In this example, the motor 1050 is for mounting on a support, such as described in respect of FIGS. 4A, 4B, 9A, 9B, or the like, and is coupled to an occluder 1010 which, in use, is positioned in the field of view of a subject's second eye, and preferably, an amblyopic eye.

In particular, the motor includes a housing 1051, a crank 1052, and a crank shaft 1054 extending perpendicularly from the crank 1052, which in this example is coupled to the occluder 1010 via an intermediary member 1053. The occluder 1010 and the intermediary arm 1053 are integrally formed, however in other examples may be separately formed and attached together.

In any event, in use the DC motor 1050 receives power and control signals from power supply and controller respectively. The motor 1050 converts the power to mechanical rotary motion of the crank 1052, which in turn rotates the crank shaft 1054, in accordance with the control signals. The crank shaft 1054 is received within an aperature or slot of the intermediary arm 1053, such that rotaty motion of the crank shaft 1054 causes the intermediary member 1053 to move about a pivot 1055, and thus cause the occluder 1010 to move. Whilst this typically causes arcuate motion of the occluder 1010, this will nonetheless be perceived as at substantially linear, vertical movement in the field of view of the subject's amblyopic eye.

It will be appreciated that the power supply and/or controller (not shown) may be provided in the housing 1051, or external to the housing such as described with reference to FIGS. 9A and 9B.

Figure 11A:
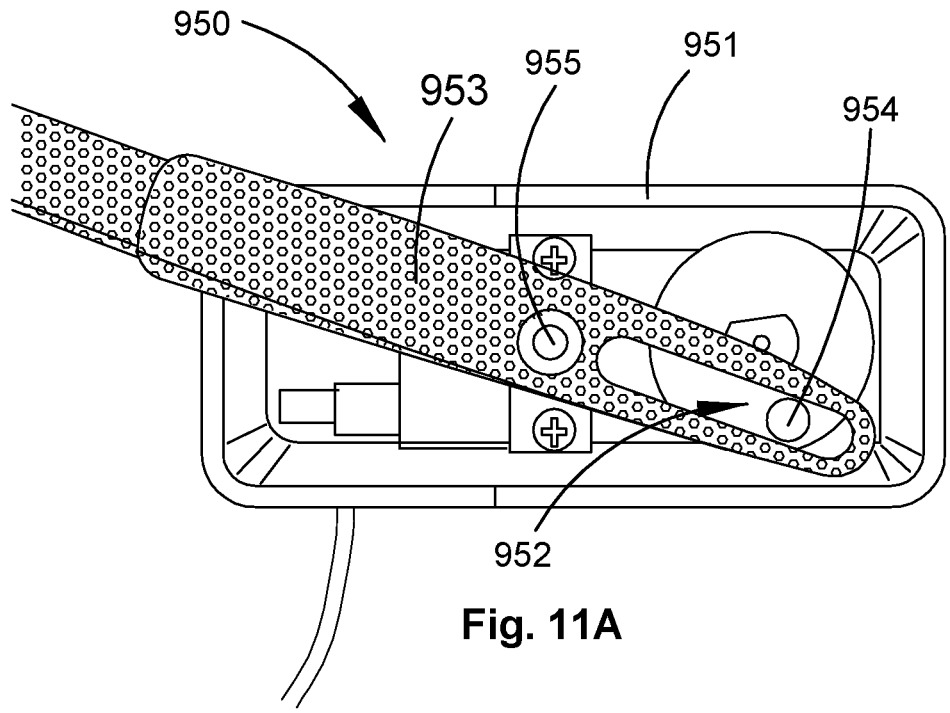
FIG. 11A is an internal, side view of the motor of FIG. 9A.
Figure 11B:
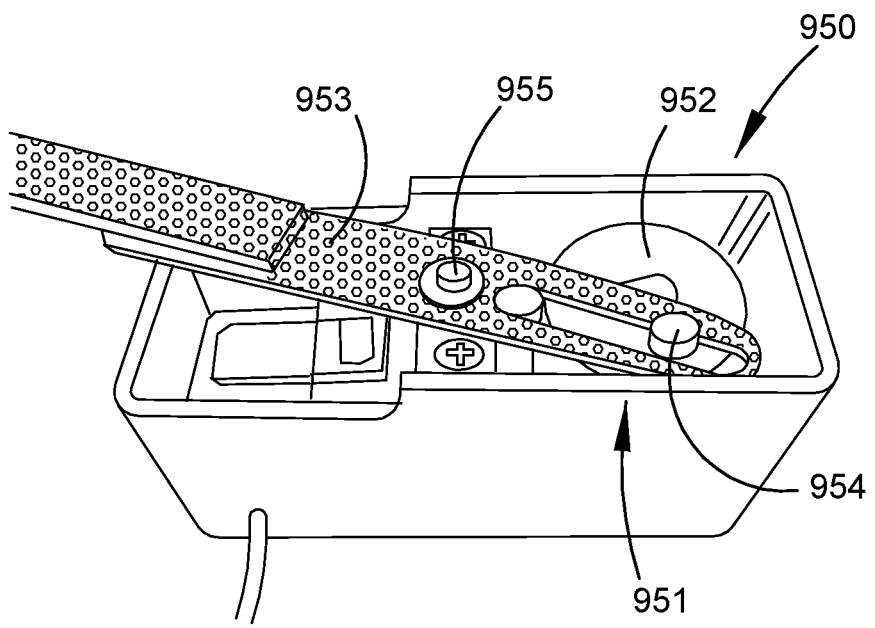
FIG. 11B is an internal, perspective view of the motor of FIG. 9A.

The geared DC motor 950 of the example shown in FIGS. 9A and 9B will now be described in more detail with reference to FIGS. 11A to 11C. Features similar to those of the example described above have been assigned correspondingly similar reference numerals.

In this example, the motor 950 includes a housing 951 which houses a crank 952 and crank shaft 954. Power received from the external power supply is converted to rotary motion of the crank 952 and thus crank shaft 954 in accordance with control signals received from the external motor controller. Thus, the crank shaft 952 is received within a slot of an intermediary arm 953, and thus rotation of the shaft 952 causes the arm 953 to pivot about a pivot 955 and thereby move the opaque strip. As discussed, whilst the movement of the opaque strip actuated in this regard may be arcuate, it will typically be perceived by the subject as substantially linear movement of an occluded area within the field of view of the second eye.

Optionally, the motor 950 may include dampening, for example, internal or external to the housing 951, for dampening vibrations caused by the motor, in use. This is particularly beneficial in increasing the comfort and usability of apparatus 900.

The above describes a method and apparatus for visual training, and in one particular example, for the treatment of amblyopia. In this respect, the described method and apparatus are non-invasive, and have the advantage of providing benefit to a wide range of subjects including subjects of a range of ages.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

Persons skilled in the art will appreciate that numerous variations and modifications will become apparent. All such variations and modifications which become apparent to persons skilled in the art, should be considered to fall within the spirit and scope that the invention broadly appearing before described. Thus, for example, it will be appreciated that features from different examples above may be used interchangeably where appropriate.

The claims defining the invention are as follows:

1. An apparatus for use in treating amblyopia of a subject, the apparatus including:
    an at least partially opaque elongate occluder for at least partially occluding an area of a field of view of a first eye in a lateral direction so as to define an occluded area and a non-occluded area, and,
    a means for moving the at least partially opaque elongate occluder,
    wherein when in use the means for moving the at least partially opaque elongate occluder causes the occluded area moves relative to the field of view in a direction perpendicular relative to the lateral direction, and the apparatus is configured to have the subject:
    a) view at least one target that extends into the occluded area using both eyes so that the subject perceives an image of the at least one target, a first image in the non-occluded area being at least partially based on signals from the first eye and a second image in the occluded area being at least partially based on signals from a second eye; and
    b) ensure the at least one target is at least partially aligned in the occluded and non-occluded areas.

2. The apparatus of claim 1, wherein the apparatus includes a support including at least one of:
    a) a pair of spectacles,
    b) a hat, and
    c) a headband.

3. The apparatus of claim 1, wherein the at least partially opaque elongate occluder defines an at least partially opaque region.

4. The apparatus of claim 3, wherein the means for moving the at least partially opaque elongate occluder includes:
    a) one or more displays including a plurality of pixels,
    b) each pixel is in any one of a first state and a second state, wherein in the first state the pixel is at least partially opaque, and in the second state the pixel is transparent, and
    c) wherein the at least partially opaque region is defined by one or more pixels in the first state, and wherein the apparatus selectively controls the plurality of pixels thereby to selectively control the at least partially opaque region.

5. The apparatus of claim 4, wherein each display includes:
    a) one or more display elements supported in series across at least part of the field of view;
    b) each display element includes a plurality of pixel elements; and
    c) wherein each pixel includes a pixel element from each of the one or more display elements.

6. The apparatus of claim 3, wherein the apparatus includes a safety barrier mounted between the at least partially opaque region and the eyes of the subject.

7. The apparatus of claim 1, wherein the apparatus includes a switch that in use allows the subject to toggle the apparatus between an operative and an inoperative state, wherein in the inoperative state the field of view is not occluded.

8. The apparatus of claim 3, the apparatus including a controller for controlling a position of the at least partially opaque region relative to the first eye.

9. The apparatus of claim 1, wherein the apparatus includes an electronic processing system, the electronic processing system is configured for:
    a) determining a visual training procedure; and,
    b) controlling a controller in accordance with the determined visual training procedure.

10. A method for use in treating amblyopia of a subject, the method including:
    a) at least partially occluding an area of a field of view of a first eye in a lateral direction so as to define an occluded area and a non-occluded area;
    b) moving the occluded area relative to the field of view in a direction perpendicular relative to the lateral direction;

c) viewing at least one target that extends into the occluded area using both eyes so that the subject perceives an image of the at least one target, a first image in the non-occluded area being at least partially based on signals from the first eye and a second image in the occluded area being at least partially based on signals from a second eye;

d) ensuring the at least one target is at least partially aligned in the occluded and non-occluded areas; and e) treating the second eye of the subject, wherein the second eye is amblyopic.

11. The method of claim 10, wherein the method includes relatively moving the at least one target and the field of view of the subject, wherein relatively moving the at least one target and the field of view is achieved by any one of:

a) a movement of the subject, b) a movement of part of the subject, c) a movement of the eyes of the subject, and d) a movement of the at least one target.

12. The method of claim 11, wherein moving the occluded area is achieved by any one of:

a) a movement of the subject, and b) a movement of the occluded area relative to the first eye.

13. The method of claim 10, wherein the method includes oscillating the occluded area substantially within the field of view, and wherein a period of oscillation is included within any one range of:

a) 0.01 Hz to 5 Hz, b) 0.1 Hz to 2 Hz, and c) 0.5 Hz and 1.5 Hz.

14. The method of claim 10, wherein the at least one target is an elongate target, and the occluded area extends perpendicularly to the at least one target.

15. The method of claim 10, wherein the occluded area is shaped substantially according to any one of:

a) a circle;

b) a square;

c) a rectangle;

d) an elongate rectangle; and, e) an ellipse.

* * * * *

UNITED STATES PATENT AND TRADEMARK OFFICE
CERTIFICATE OF CORRECTION

PATENT NO. : 10,780,015 B2  
APPLICATION NO. : 14/392260  
DATED : September 22, 2020  
INVENTOR(S) : Christopher Bunker Page 1 of 1

It is certified that error appears in the above-identified patent and that said Letters Patent is hereby corrected as shown below:

In the Claims

At Column 17 and 18, Lines 67 and 1, change, "causes the occluded area moves relative to the field" to --causes the occluded area to move relative to the field--

Signed and Sealed this  
Thirty-first Day of August, 2021

Drew Hirshfeld  
*Performing the Functions and Duties of the*  
*Under Secretary of Commerce for Intellectual Property and*  
*Director of the United States Patent and Trademark Office*